(12) United States Patent
Williams et al.

(10) Patent No.: US 7,285,287 B2
(45) Date of Patent: Oct. 23, 2007

(54) CARBON DIOXIDE-ASSISTED METHODS OF PROVIDING BIOCOMPATIBLE INTRALUMINAL PROSTHESES

(75) Inventors: Michael S. Williams, Santa Rosa, CA (US); Joseph M. DeSimone, Chapel Hill, NC (US)

(73) Assignee: SyneCor, LLC, Windsor, CA (US)

( * ) Notice: Subject to any disclaimer, the term of this patent is extended or adjusted under 35 U.S.C. 154(b) by 269 days.

(21) Appl. No.: 10/662,621

(22) Filed: Sep. 15, 2003

(65) Prior Publication Data

US 2004/0098120 A1    May 20, 2004

Related U.S. Application Data

(60) Provisional application No. 60/426,126, filed on Nov. 14, 2002.

(51) Int. Cl.
*A61L 29/00*  (2006.01)
(52) U.S. Cl. .................. 424/423; 424/700; 623/1.11; 623/1.12; 623/1.15; 623/1.38
(58) Field of Classification Search ............... 424/405, 424/406, 423–428, 430, 484–488, 700, 433; 623/1.11–1.54, 901; 264/88
See application file for complete search history.

(56) References Cited

U.S. PATENT DOCUMENTS

| | | | |
|---|---|---|---|
| 4,351,337 A | 9/1982 | Sidman | 128/260 |
| 4,975,280 A | 12/1990 | Schacht et al. | 424/428 |
| 4,994,033 A | 2/1991 | Shockey et al. | 604/101.02 |
| 5,059,211 A | 10/1991 | Stack et al. | 623/1.15 |
| 5,085,629 A | 2/1992 | Goldberg et al. | 604/8 |
| 5,271,400 A | 12/1993 | Dumoulin et al. | 128/653.2 |
| 5,306,286 A | 4/1994 | Stack et al. | 623/1.12 |
| 5,340,614 A | 8/1994 | Perman et al. | 427/2.24 |
| 5,423,885 A | 6/1995 | Williams | 623/1.17 |
| 5,443,458 A | 8/1995 | Eury | 604/891.1 |
| 5,443,498 A | 8/1995 | Fontaine | 623/1 |
| 5,443,500 A | 8/1995 | Sigwart | 623/1 |
| 5,449,382 A | 9/1995 | Dayton | 623/1 |
| 5,456,917 A | 10/1995 | Wise et al. | 424/426 |
| 5,464,419 A | 11/1995 | Glastra | |
| 5,500,013 A | 3/1996 | Buscemi et al. | 623/1 |
| 5,508,060 A | 4/1996 | Perman et al. | 427/2.14 |

(Continued)

FOREIGN PATENT DOCUMENTS

EP      0405284 A2    6/1990

(Continued)

OTHER PUBLICATIONS

Cooper, Andrew I., "Polymer Synthesis and Processing Using Supercritical Carbon Dioxide", *Journal of Materials Chemistry* 10, pp. 207-234 (2000).

(Continued)

*Primary Examiner*—Neil S. Levy
(74) *Attorney, Agent, or Firm*—Myers Bigel Sibley & Sajovec, P.A.

(57) ABSTRACT

Methods of producing biocompatible intraluminal prostheses are provided and include immersing polymeric material of an intraluminal prosthesis in a densified carbon dioxide composition under controlled conditions such that toxic materials are absorbed by the densified carbon dioxide composition.

15 Claims, 1 Drawing Sheet

U.S. PATENT DOCUMENTS

| | | | | |
|---|---|---|---|---|
| 5,527,337 A | 6/1996 | Stack et al. | ............ | 606/198 |
| 5,545,208 A | 8/1996 | Wolff et al. | ............ | 623/1 |
| 5,551,954 A | 9/1996 | Buscemi et al. | ............ | 623/1 |
| 5,591,199 A | 1/1997 | Porter | ............ | 606/198 |
| 5,591,224 A | 1/1997 | Schwartz et al. | ............ | 623/1 |
| 5,591,227 A | 1/1997 | Dinh et al. | ............ | 623/1 |
| 5,605,696 A | 2/1997 | Eury et al. | ............ | 424/423 |
| 5,607,467 A | 3/1997 | Froix | ............ | 623/1 |
| 5,618,299 A | 4/1997 | Khosravi et al. | ............ | 606/198 |
| 5,629,077 A | 5/1997 | Turnlund et al. | ............ | 623/1.15 |
| 5,649,952 A | 7/1997 | Lam | ............ | 606/198 |
| 5,670,161 A | 9/1997 | Healy et al. | ............ | 424/426 |
| 5,674,192 A | 10/1997 | Sahatian et al. | ............ | 604/28 |
| 5,697,967 A | 12/1997 | Dinh et al. | ............ | 623/1 |
| 5,723,508 A | 3/1998 | Healy et al. | ............ | 521/61 |
| 5,733,327 A | 3/1998 | Igaki et al. | ............ | 623/1 |
| 5,733,328 A | 3/1998 | Fordenbacher | ............ | 623/1.16 |
| 5,733,330 A | 3/1998 | Cox | ............ | 623/1 |
| 5,741,293 A | 4/1998 | Wijay | ............ | 623/1.15 |
| 5,741,323 A | 4/1998 | Pathak et al. | ............ | 623/1 |
| 5,744,958 A | 4/1998 | Werne | ............ | 324/318 |
| 5,746,208 A | 5/1998 | Prince | ............ | 128/653.4 |
| 5,749,922 A | 5/1998 | Slepian et al. | ............ | 623/1 |
| 5,762,065 A | 6/1998 | Prince | ............ | 128/653.4 |
| 5,762,625 A | 6/1998 | Igaki | ............ | 604/8 |
| 5,766,204 A | 6/1998 | Porter | ............ | 606/198 |
| 5,766,710 A | 6/1998 | Turnlund et al. | ............ | 428/36.1 |
| 5,769,883 A | 6/1998 | Buscemi et al. | ............ | 623/1 |
| 5,770,645 A | 6/1998 | Stamler et al. | ............ | 524/419 |
| 5,792,056 A | 8/1998 | Prince | ............ | 600/420 |
| 5,799,649 A | 9/1998 | Prince | ............ | 128/653.4 |
| 5,800,507 A | 9/1998 | Schwartz | ............ | 623/1 |
| 5,824,049 A | 10/1998 | Ragheb et al. | ............ | 623/1 |
| 5,851,217 A | 12/1998 | Wolff et al. | ............ | 606/191 |
| 5,860,467 A | 1/1999 | DeSimone et al. | ............ | 164/5 |
| 5,868,781 A | 2/1999 | Killion | ............ | 623/1.15 |
| 5,873,904 A | 2/1999 | Ragheb et al. | ............ | 623/1 |
| 5,916,585 A | 6/1999 | Cook et al. | ............ | 424/426 |
| 5,924,987 A | 7/1999 | Meaney et al. | ............ | 600/420 |
| 5,957,971 A | 9/1999 | Schwartz | ............ | 623/1 |
| 5,957,975 A | 9/1999 | Lafont et al. | ............ | 623/1 |
| RE36,370 E | 11/1999 | Li | ............ | 424/443 |
| 5,980,564 A | 11/1999 | Stinson | ............ | 623/1 |
| 5,984,957 A | 11/1999 | Laptewicz, Jr. et al. | ... | 623/1.15 |
| 5,984,963 A | 11/1999 | Ryan et al. | ............ | 623/12 |
| 6,004,346 A | 12/1999 | Wolff et al. | ............ | 623/1 |
| 6,045,568 A | 4/2000 | Igaki et al. | ............ | 606/198 |
| 6,071,439 A * | 6/2000 | Bawa et al. | ............ | 264/1.1 |
| 6,080,177 A | 6/2000 | Igaki et al. | ............ | 606/198 |
| 6,080,190 A | 6/2000 | Schwartz | ............ | 623/1 |
| 6,096,070 A | 8/2000 | Ragheb et al. | ............ | 623/1 |
| 6,113,628 A | 9/2000 | Borghi | ............ | 623/1.016 |
| 6,120,847 A | 9/2000 | Yang et al. | ............ | 427/335 |
| 6,139,511 A | 10/2000 | Huter et al. | ............ | 600/585 |
| 6,156,062 A | 12/2000 | McGuinness | ............ | 623/1.11 |
| 6,165,196 A | 12/2000 | Stack et al. | ............ | 606/194 |
| 6,174,330 B1 | 1/2001 | Stinson | ............ | 623/1.34 |
| 6,176,871 B1 | 1/2001 | Pathak et al. | ............ | 623/1 |
| 6,179,867 B1 | 1/2001 | Cox | ............ | 623/1.15 |
| 6,224,626 B1 | 5/2001 | Steinke | ............ | 623/1.16 |
| 6,232,434 B1 | 5/2001 | Stamler et al. | ............ | 528/373 |
| 6,240,311 B1 | 5/2001 | Prince | ............ | 600/420 |
| 6,240,936 B1 | 6/2001 | DeSimone et al. | ............ | 134/33 |
| 6,245,103 B1 | 6/2001 | Stinson | ............ | 623/1.22 |
| 6,251,136 B1 | 6/2001 | Guruwaiya et al. | ............ | 623/1.46 |
| 6,264,671 B1 | 7/2001 | Stack et al. | ............ | 606/198 |
| 6,264,683 B1 | 7/2001 | Stack et al. | ............ | 623/1.11 |
| 6,267,769 B1 | 7/2001 | Truwit | ............ | 606/130 |
| 6,272,370 B1 | 8/2001 | Gillies et al. | ............ | 600/411 |
| 6,298,902 B1 | 10/2001 | DeSimone et al. | ............ | 164/131 |
| 6,299,604 B1 | 10/2001 | Ragheb et al. | ............ | 604/265 |
| 6,302,907 B1 | 10/2001 | Hijlkema | ............ | 623/1.16 |
| 6,306,422 B1 | 10/2001 | Batich et al. | ............ | 424/423 |
| 6,312,457 B1 | 11/2001 | DiMatteo et al. | ............ | 623/1.13 |
| 6,322,490 B1 | 11/2001 | Stack et al. | ............ | 600/3 |
| 6,323,256 B1 | 11/2001 | DelMain | ............ | 523/112 |
| 6,368,346 B1 | 4/2002 | Jadhav | ............ | 623/1.22 |
| 6,387,124 B1 | 5/2002 | Buscemi et al. | ............ | 623/1.15 |
| 6,413,272 B1 | 7/2002 | Igaki | ............ | 623/1.15 |
| 6,420,397 B1 | 7/2002 | Pan et al. | ............ | 514/352 |
| 6,436,132 B1 | 8/2002 | Patel et al. | ............ | 523/1.13 |
| 6,440,405 B1 | 8/2002 | Cooper et al. | ............ | 424/78.17 |
| 6,451,373 B1 | 9/2002 | Hossainy et al. | ............ | 427/2.25 |
| 6,463,317 B1 | 10/2002 | Kucharczyk et al. | ............ | 600/411 |
| 6,463,318 B2 | 10/2002 | Prince | ............ | 600/420 |
| 6,468,299 B2 | 10/2002 | Stack et al. | ............ | 623/1.11 |
| 6,468,519 B1 | 10/2002 | Uhrich | ............ | 424/78.01 |
| 6,627,246 B2 * | 9/2003 | Mehta et al. | ............ | 427/2.1 |
| 2001/0020083 A1 | 9/2001 | Stamler et al. | ............ | 528/373 |
| 2001/0021871 A1 | 9/2001 | Stinson | ............ | 623/1.15 |
| 2001/0029398 A1 | 10/2001 | Jadhav | ............ | 623/1.22 |
| 2001/0037126 A1 | 11/2001 | Stack et al. | ............ | 606/191 |
| 2001/0044630 A1 | 11/2001 | Stack et al. | ............ | 606/108 |
| 2001/0051822 A1 | 12/2001 | Stack et al. | ............ | 623/1.11 |
| 2002/0013617 A1 | 1/2002 | Matsutani et al. | ............ | 623/1.15 |
| 2002/0042625 A1 | 4/2002 | Stack et al. | ............ | 606/194 |
| 2002/0051845 A1 | 5/2002 | Mehta et al. | ............ | 427/2.1 |
| 2002/0077691 A1 | 6/2002 | Nachtigall | ............ | 623/1.12 |
| 2002/0124626 A1 | 9/2002 | Ching et al. | ............ | 72/416 |
| 2002/0138133 A1 | 9/2002 | Lenz et al. | ............ | 623/1.15 |
| 2002/0155025 A1 | 10/2002 | Daum | ............ | 420/585 |
| 2002/0188342 A1 | 12/2002 | Rykhus | ............ | 623/1.2 |
| 2003/0044514 A1 * | 3/2003 | Richard | ............ | 427/2.1 |
| 2003/0105516 A1 | 6/2003 | Austin | ............ | 623/1.16 |

FOREIGN PATENT DOCUMENTS

| | | |
|---|---|---|
| EP | 0693923 B1 | 10/2000 |
| WO | WO/99/59548 | 11/1999 |

OTHER PUBLICATIONS

Engwicht et al., "Characterization of Co-Polymers of Lactic and Glycolic Acid for Supercritical Fluid Processing", *Biomaterials* 21, pp. 1587-1593 (2000).

Herberger et al., "Carbon Dioxide Extraction Of Residual Solvents In Poly(lactide-co-glycolide) Microparticles", *Journal of Controlled Release* 90, pp. 181-195 (2003).

Hile et al., "Active Growth Factor Delivery From Poly(D,L-lactide-co-glycolide) Foams Prepared In Supercritical $CO_2$", *Journal of Controlled Release* 66, pp. 177-185 (2000).

Mooney et al., "Novel Approach to Fabricate Porous Sponges of Poly(D,L-lactic-co-glycolic acid) without the use of organic solvents", *Biomaterials*, vol. 17, No. 14, pp. 1417-1422 (1996).

Shakesheff, Kevin "Gently Does It", *Chemistry in Britain*, pp. 30-32 (2003).

Wood et al., "Structural Control In Polymeric Materials Using Supercritical Carbon Dioxide", http://www.liv.ac.uk/~aicooper/Bath_2001.pdf.

International Search Report for Int'l Appl'n. No. PCT/US03/33645.

* cited by examiner

CARBON DIOXIDE-ASSISTED METHODS OF PROVIDING BIOCOMPATIBLE INTRALUMINAL PROSTHESES

RELATED APPLICATION

This application claims the benefit of U.S. Provisional Application No. 60/426,126, filed Nov. 14, 2002, the disclosure of which is incorporated herein by reference in its entirety as if set forth fully herein.

FIELD OF THE INVENTION

The present invention relates generally to medical devices and, more particularly, to methods of providing biocompatible medical devices.

BACKGROUND OF THE INVENTION

Stents are typically used as adjuncts to percutaneous transluminal balloon angioplasty procedures, in the treatment of occluded or partially occluded arteries and other blood vessels. As an example of a balloon angioplasty procedure, a guiding catheter or sheath is percutaneously introduced into the cardiovascular system of a patient through the femoral arteries and advanced through the vasculature until the distal end of the guiding catheter is positioned at a point proximal to the lesion site. A guidewire and a dilatation catheter having a balloon on the distal end are introduced through the guiding catheter with the guidewire sliding within the dilatation catheter. The guidewire is first advanced out of the guiding catheter into the patient's vasculature and is directed across the arterial lesion. The dilatation catheter is subsequently advanced over the previously advanced guidewire until the dilatation balloon is properly positioned across the arterial lesion. Once in position across the lesion, the expandable balloon is inflated to a predetermined size with a radiopaque liquid at relatively high pressure to radially compress the atherosclerotic plaque of the lesion against the inside of the artery wall and thereby dilate the lumen of the artery. The balloon is then deflated to a small profile so that the dilatation catheter can be withdrawn from the patient's vasculature and blood flow resumed through the dilated artery.

Balloon angioplasty sometimes results in short or long term failure (restenosis). That is, vessels may abruptly close shortly after the procedure or restenosis may occur gradually over a period of months thereafter. To counter restenosis following angioplasty, implantable intraluminal prostheses, commonly referred to as stents, are used to achieve long term vessel patency. A stent functions as scaffolding to structurally support the vessel wall and thereby maintain luminal patency, and are transported to a lesion site by means of a delivery catheter.

Types of stents may include balloon expandable stents, spring-like, self-expandable stents, and thermally expandable stents. Balloon expandable stents are delivered by a dilitation catheter and are plastically deformed by an expandable member, such as an inflation balloon, from a small initial diameter to a larger expanded diameter. Self-expanding stents are formed as spring elements which are radially compressible about a delivery catheter. A compressed self-expanding stent is typically held in the compressed state by a delivery sheath. Upon delivery to a lesion site, the delivery sheath is retracted allowing the stent to expand. Thermally expandable stents are formed from shape memory alloys which have the ability to expand from a small initial diameter to a second larger diameter upon the application of heat to the alloy.

Polymeric materials are increasingly being utilized in intraluminal prostheses, such as stents, as well as in other types of medical devices used within the bodies of subjects. Polymeric materials conventionally utilized in the medical device industry for implantation within the bodies of subjects include, but are not limited to polyurethanes, polyolefins (e.g., polyethylene and polypropylene), poly(meth)acrylates, polyesters (e.g., polyethyleneterephthalate), polyamides, polyvinyl resins, silicon resins (e.g., silicone rubbers and polysiloxanes), polycarbonates, polyfluorocarbon resins, synthetic resins, and polystyrene.

Many conventional polymeric materials contain a range of additives (e.g., plasticizers, antioxidants, UV stabilizers, etc.) as well as a host of contaminants (e.g., residual monomer, oligomers, solvent residues, catalysts, initiators, etc.). For example, casting solvents such as dimethyl sulfoxide (DMSO), chloro-organics, aromatics, tetrahydrofuran (THF), etc. are conventionally utilized in stent production. Moreover, various toxic organic solvents and plasticizers are conventionally used to impregnate the polymeric material of implantable devices, such as intraluminal prostheses, with pharmacological agents. Trace quantities of these materials may remain in the polymeric materials during fabrication of these devices and patients receiving these devices, or pharmacological agents eluted therefrom, may be exposed to these potentially toxic materials, particularly when the implantable device erodes.

As such, it is desirable to purify polymeric materials utilized in medical devices, such as intraluminal prostheses, in order to remove solvents and other potentially toxic materials and to enhance the biocompatibility of the polymeric material. Unfortunately, conventional purification methods may involve applying heat to the polymeric material. The addition of heat may alter the physical characteristics of the polymeric material, thus negatively affecting the biocompatibility of the material.

SUMMARY OF THE INVENTION

Methods of producing biocompatible intraluminal prostheses according to embodiments of the present invention utilize densified carbon dioxide to remove toxic materials. According to embodiments of the present invention, the polymeric material of an intraluminal prosthesis is immersed in a densified carbon dioxide composition to absorb toxic materials (e.g., organic solvents (polar or non-polar), unpolymerized monomers, polymerization catalysts, and polymerization initiators, etc.) therefrom. The term "toxic materials" includes all types of foreign materials, contaminants, chemicals, physical impurities, and the like, without limitation, that may be harmful to a subject. The densified carbon dioxide composition containing the toxic materials is then removed (completely or partially) from the polymeric material and the toxic materials are easily be separated from the carbon dioxide composition by decreasing the density of the carbon dioxide.

DETAILED DESCRIPTION OF THE INVENTION

Figure 1:
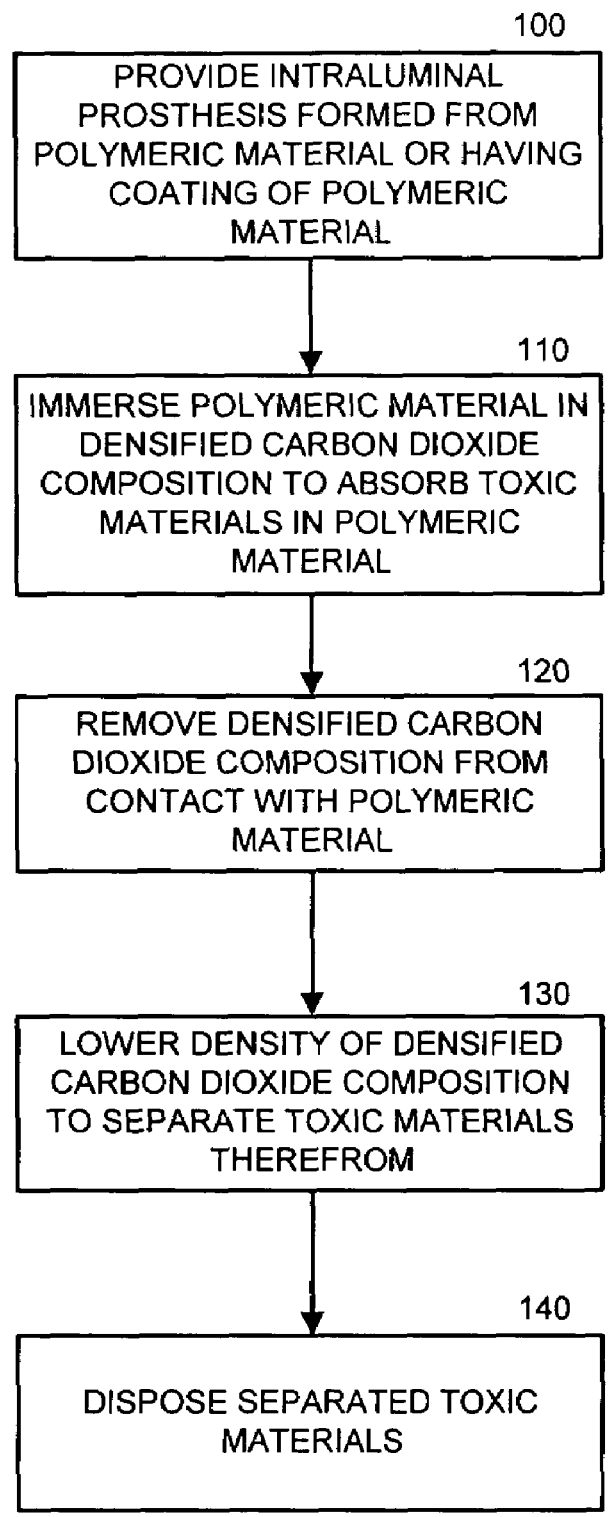
FIG. 1 is a flowchart of operations for impregnating polymeric material with pharmacological agents, according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

The term "biocompatible" as used herein, is intended to denote a material that upon contact with a living element such as a cell or tissue, does not cause toxicity.

The term "dosage regimen" is used herein to describe both exogenously administered and internally administered pharmacological agents. A dosage regimen includes both an amount of a pharmacological agent and time(s) that each dose is to be taken. A dosage regimen may also indicate whether a pharmacological agent is to be taken with food or not, and whether other pharmacological agents are to be avoided.

The term "eluting" is used herein to mean the release of a pharmacological agent from a polymeric material. Eluting may also refer to the release of a material from a substrate via diffusional mechanisms or by release from a polymeric material/substrate as a result of the breakdown or erosion of the material/substrate.

The term "erodible" as used herein refers to the ability of a material to maintain its structural integrity for a desired period of time, and thereafter gradually undergo any of numerous processes whereby the material substantially loses tensile strength and mass. Examples of such processes comprise enzymatic and non-enzymatic hydrolysis, oxidation, enzymatically-assisted oxidation, and others, thus including bioresorption, dissolution, and mechanical degradation upon interaction with a physiological environment into components that the patient's tissue can absorb, metabolize, respire, and/or excrete. The terms "erodible" and "degradable" are intended to be used herein interchangeably.

The term "hydrophobic" is used herein to mean not soluble in water.

The term "hydrophilic" is used herein to mean soluble in water.

The term "lumen" is used herein to mean any inner open space or cavity of a body passageway.

The terms "polymer" and "polymeric material" are synonymous and are to be broadly construed to include, but not be limited to, homopolymers, copolymers, terpolymers, and the like.

The term "prosthesis" is used herein in a broad sense to denote any type of intraluminal prosthesis or other device which is implanted in the body of a subject for some therapeutic reason or purpose including, but not limited to stents, drug delivery devices, etc.

The term "subject" is used herein to describe both human beings and animals (e.g., mammalian subjects) for medical, veterinary, testing and/or screening purposes.

The term "toxic materials" is intended to include all types of foreign materials, contaminants, chemicals, physical impurities, and the like, without limitation, that may be harmful to a subject.

As used herein, phrases such as "between X and Y" and "between about X and Y" should be interpreted to include X and Y.

As used herein, phrases such as "between about X and Y" mean "between about X and about Y."

As used herein, phrases such as "from about X to Y" mean "from about X to about Y."

Referring now to FIG. 1, methods of producing biocompatible intraluminal prostheses (e.g., stents, etc.), according to embodiments of the present invention are illustrated. Embodiments of the present invention can be employed in conjunction with a number of manufacturing processes associated with producing intraluminal prostheses including, but not limited to, extrusion, pultrusion, injection molding, etc. Moreover, embodiments of the present invention may be utilized in batch, semicontinuous, or continuous processes.

An intraluminal prosthesis (e.g., a stent, drug delivery device, etc.) comprising polymeric material (e.g., formed from polymeric material, or having a partial or complete coating of polymeric material) is provided (Block 100). The polymeric material may contain trace amounts of one or more toxic materials as a result of previous fabrication steps. For example, residual amounts of various casting solvents including, but not limited to, organic solvents (polar or non-polar) such as DMSO, dimethyl acetimide (DMAc), dimethyl foramide (DMF), chloro-organics, aromatics (such as benzene, toluene, xylene, chlorobenzene), THF, TFF, diglyac glycol, esters, etc. may be present, as would be understood by one skilled in the art. In addition, unpolymerized monomers, oligomers, polymerization initiators, catalysts, etc. may be present, as would be understood by one skilled in the art. Oligomers are undesired, low molecular weight molecules that may be linear or cyclic.

According to embodiments of the present invention, levels of toxic materials can be reduced to predetermined, acceptable values in parts per million (ppm) based upon specific toxic materials. For example, toxic material "A" that is present in the polymeric material of an intraluminal prosthesis at levels of from greater than 200, 400, 600, 800 or 1,000 ppm, may be reduced to "acceptable" values of, for example, 20, 50, 100, 200, or 400 ppm, etc.

Exemplary polymeric materials that may be utilized in intraluminal prostheses (and in accordance with embodiments of the present invention) include, but are not limited to, polyurethanes, polyolefins, poly(meth)acrylates, polyesters, polyamides, polyvinyl resins, silicon resins, polycarbonates, polyfluorocarbon resins, synthetic resins, and polystyrene. In addition, polymeric material of intraluminal prostheses may be erodible (or an intraluminal prosthesis may have an erodible coating) or non-erodible (or an intraluminal prosthesis may have a non-erodible coating).

Intraluminal prostheses according to embodiments of the present invention, may be formed from various materials. In addition, intraluminal prostheses having polymeric coatings, according to embodiments of the present invention, may be metallic prostheses or polymeric prostheses.

Exemplary erodible materials that may be utilized in intraluminal prostheses (and in accordance with embodiments of the present invention) include, but are not limited to, surgical gut, silk, cotton, liposomes, poly(hydroxybutyrate), polycarbonates, polyacrylates, polyanhydrides, polyethylene glycol, poly(ortho esters), poly(phosphoesters), polyesters, polyamides (such as polyamides derived from D-glucose), polyphosphazenes, poly(p-dioxane), poly(amino acid), polyglactin, and copolymers thereof, erodible hydrogels, natural polymers such as collagen and chitosan, etc. See, e.g., U.S. Pat. No. 5,723,508 to Healy et al. Particular examples of suitable erodible polymers include, but are not limited to, aliphatic polyester polymers such as poly(lactic acid), poly(L-lactic acid), poly(D,L-lactic acid), poly(glycolic acid), poly(D-lactic-co-glycolic acid), poly(L-lactic-co-glycolic acid), poly (D,L-lactic-co-glycolic acid), poly($\epsilon$-caprolactone), poly(valerolactone), poly(hydroxy butyrate) (including poly(hydroxy butyrate valerate)), poly (hydrovalerate), polydioxanone, poly(propylene fumarate), etc., including copolymers thereof such as polylactic acid-polyethylene glycol block copolymer, and poly(ethyleneoxide)-poly(butylenetetraphthalate), poly(lactic acid-co-lysine), poly($\epsilon$-caprolactone copolymers), poly(L-lactic acid copolymers), etc. See, e.g., J. Oh et al., PCT Application WO 99/59548 at page 2. Additional examples of erodible polymers are set forth in U.S. Pat. No. 5,916,585 to Cook et al. at col. 9 line 53 to col. 10 line 22. The molecular weight (that is, average molecular weight) of the polymer may be from 1,000, 10,000, 100,000 or 500,000 to 2,000,000 or 4,000,000 Daltons, or more. Exemplary non erodible materials that may be utilized in intraluminal prostheses (and in accordance with embodiments of the present invention) include, but are not limited to, fluoropolymers, polyesters, PET, polyethylenes, polypropylenes, etc., and/or ceramics, such as hydroxyapetite.

Moreover, intraluminal prostheses may include various pharmacological agents. In general, pharmacological agents suitable for inclusion in prosthesis materials and/or coatings (and according to embodiments of the present invention) include, but are not limited to, drugs and other biologically active materials, and may be intended to perform a variety of functions, including, but not limited to: anti-cancer treatment (e.g., Resan), anti-clotting or anti-platelet formation, the prevention of smooth muscle cell growth, migration, proliferation within a vessel wall. Pharmacological agents may include antineoplastics, antimitotics, antiinflammatories, antiplatelets, anticoagulants, antifibrins, antithrombins, antiproliferatives, antibiotics, antioxidants, and antiallergic substances as well as combinations thereof. Examples of antineoplastics and/or antimitotics include paclitaxel (cytostatic and ant-inflammatory) and it's analogs and all compounds in the TAXOL® (Bristol-Myers Squibb Co., Stamford, Conn.) family of pharmaceuticals, docetaxel (e.g., TAXOTERE® from Aventis S. A., Frankfurt, Germany) methotrexate, azathioprine, vincristine, vinblastine, fluorouracil, doxorubicin hydrochloride (e.g., ADRIAMYCIN® from Pharmacia & Upjohn, Peapack N.J.), and mitomycin (e.g., MUTAMYCIN® from Bristol-Myers Squibb Co., Stamford, Conn.). Examples of antiinflammatories include Sirolimus and it's analogs (including but not limited to Everolimus and all compounds in the Limus family of pharmaceuticals), glucocorticoids such as dexamethasone, methylprednisolone, hydrocortisone and betamethasone and non-steroidal antiinflammatories such as aspirin, indomethacin and ibuprofen. Examples of antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.) Examples of cytostatic or antiproliferative agents or proliferation inhibitors include everolimus, actinomycin D, as well as derivatives and analogs thereof (manufactured by Sigma-Aldrich, Milwaukee, Wis.; or COSMEGEN® available from Merck & Co., Inc., Whitehouse Station, N.J.), angiopeptin, angiotensin converting enzyme inhibitors such as captopril (e.g., CAPOTEN® and CAPOZIDE® from Bristol-Myers Squibb Co., Stamford, Conn.), cilazapril or lisinopril (e.g., Prinivilo and PRINZIDE® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name MEVACOR® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents that may be used include alphainterferon, genetically engineered epithelial cells, and dexamethasone.

U.S. Pat. No. 4,994,033 to Shockey et al.; U.S. Pat. No. 5,674,192 to Sahatian et al. and U.S. Pat. No. 5,545,208 to Wolff et al. disclose catheters comprising absorbable/biodegradable polymers or hydrogels containing the desired dosage of a drug. Stents incorporating drug delivery may be found, for example, in U.S. Pat. No. 5,766,710 to Turnlund et al.; U.S. Pat. No. 5,769,883 to Buscemi et al.; U.S. Pat. No. 5,605,696 to Eury et al.; U.S. Pat. No. 5,500,013 to Buscemi et al.; U.S. Pat. No. 5,551,954 to Buscemi et al. and U.S. Pat. No. 5,443,458 to Eury, each of which is incorporated herein by reference in its entirety.

Referring back to FIG. 1, the polymeric material of an intraluminal prosthesis is immersed in a densified (e.g., liquid or supercritical) carbon dioxide composition for a time sufficient, and under controlled conditions, to cause the trace amounts of toxic materials to be absorbed by the densified carbon dioxide composition (Block 110). Carbon dioxide is non-toxic, non-flammable, chemically inert, completely recoverable, abundant and inexpensive. Carbon dioxide has properties that are between those of many liquids and gases. At room temperature and above its vapor pressure, carbon dioxide exists as a liquid with a density comparable to organic solvents but with excellent wetting properties and a very low viscosity. Above its critical temperature and pressure (31° C. and 73.8 bar), carbon dioxide is in the supercritical state and has gas-like viscosities and liquid-like densities. Small changes in temperature or pressure cause dramatic changes in the density, viscosity, and dielectric properties of supercritical carbon dioxide, making it an unusually tunable, versatile, and selective solvent.

The densified carbon dioxide composition, according to embodiments of the present invention, may be heterogeneous or homogeneous in composition, i.e., may be a single phase composition or contain one or more additional phases, such as in the form of a microemulsion, emulsion, dispersion, suspension, etc. The densified carbon dioxide composition may comprise, consist of, or consist essentially of carbon dioxide. Where multiple phases are found in the densified carbon dioxide composition, the carbon dioxide may be in the continuous phase.

One or more other ingredients may be included in the densified carbon dioxide composition, such as co-solvents (i.e., water or organic co-solvents such as ethanol and methanol), surfactants or the like may be included. Where one or more organic co-solvents are included, it or they may be polar or nonpolar (or at least one of each). Where one or more surfactants are included it or they may comprise a carbon dioxide-philic group coupled to either a lipophilic or hydrophilic group, a conventional surfactant comprising a liphophilic group coupled to a hydrophilic group, or one or more of each. The densified carbon dioxide composition may comprise at least 30, 40, 50, 60, 70, 80 or 90 percent by weight of carbon dioxide. When water is present in the densified carbon dioxide composition, the water may comprise from about 0.01, 0.1, or 0.5 to about 1, 5, 10 or 20 percent by weight of the composition, or more.

Immersing the polymeric material of the intraluminal prosthesis in the densified carbon dioxide composition under controlled conditions includes, but is not limited to, controlling one or more of the following parameters associated with the densified carbon dioxide composition in a predetermined pattern: temperature, rate of temperature change, pressure, rate of pressure change, composition quantity, etc. Changes in one or more of these parameters (also referred to as "tuning" the densified carbon dioxide composition) can be made to selectively absorb trace amounts of toxic materials. Moreover, changes in one or more of these parameters can control both the effectiveness and efficiency of toxic material removal.

Referring back to FIG. 1, the densified carbon dioxide composition containing the toxic materials is removed from contact with the polymeric material (Block 120). Removal may include complete removal or partial removal. The density of the removed densified carbon dioxide composition is lowered such that the trace amounts of toxic materials entrained therein become separated therefrom (Block 130). The separated toxic materials are then disposed of (Block 140). The density of the removed densified carbon dioxide composition may be lowered by reducing pressure and/or increasing temperature, as would be understood by one skilled in the art.

Embodiments of the present invention described above with respect to FIG. 1 may be carried out using apparatus known to those skilled in the art. Immersing the polymeric material of an intraluminal prosthesis in a densified carbon dioxide composition for a time sufficient (Block 110) may be performed within an enclosed chamber (e.g., pressure vessel). Lowering the density of the densified carbon dioxide composition (Block 130) may also be performed within an enclosed chamber, for example an enclosed chamber separate from a chamber within which the polymeric material is immersed in the densified carbon dioxide composition.

According to embodiments of the present invention, selective removal of toxic or other materials may be accomplished via any of a variety of known masking techniques. For example, a mask may be applied to one or more portions of an intraluminal prosthesis such that toxic materials are removed only from non-masked portions of the polymeric material. Masking techniques are well understood by those skilled in the art and need not be described further herein.

Intraluminal prostheses provided in accordance with embodiments of the present invention may be employed in sites of the body other than the vasculature including, but not limited to, biliary tree, esophagus, bowels, tracheo-bronchial tree, urinary tract, etc.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed is:

1. A method of producing a biocompatible stent for in vivo use, comprising:
    providing a stent having a portion thereof formed from polymeric material selected from the group consisting of polylactic acid-polyethylene glycol block copolymer, poly(ethyleneoxide)-poly(butylenetetraphthalate), poly(lactic acid-co-lysine), a poly(L-lactic acid) copolymer and a poly($\epsilon$-caprolactone) copolymer, wherein the polymeric material contains one or more toxic materials;
    immersing the polymeric material in a densified carbon dioxide composition such that the toxic materials are absorbed by the densified carbon dioxide composition, wherein pressure and/or temperature of the densified carbon dioxide composition is adjusted to selectively absorb toxic materials from the polymeric material;
    removing the densified carbon dioxide composition containing the toxic materials from the polymeric material;
    lowering the density of the removed densified carbon dioxide composition such that the toxic materials entrained therein become separated therefrom; and
    removing the separated toxic materials, such that the stent is suitable for in vivo use.

2. A method of producing a biocompatible stent for in vivo use, comprising:
    providing a stent having a portion thereof formed from polymeric material selected from the group consisting of: poly(lactic acid), poly(L-lactic acid), poly(D,L-lactic acid), and a copolymer of poly(lactic acid), poly(L-lactic acid), and/or poly(D,L-lactic acid), wherein the polymeric material contains one or more toxic materials;
    immersing the polymeric material in a densified carbon dioxide composition such that the toxic materials are absorbed by the densified carbon dioxide composition, wherein pressure and/or temperature of the densified carbon dioxide composition is adjusted to selectively absorb toxic materials from the polymeric material;
    removing the densified carbon dioxide composition containing the toxic materials from the polymeric material;
    lowering the density of the removed densified carbon dioxide composition such that the toxic materials entrained therein become separated therefrom; and
    removing the separated toxic materials, such that the stent is suitable for in vivo use.

3. The method of claim 2, wherein the one or more toxic materials are selected from the group consisting of organic solvents (polar or non-polar), unpolymerized monomers, polymerization catalysts, oligomers, and polymerization initiators.

4. The method of claim 2, wherein the densified carbon dioxide composition is a liquid composition, and wherein the immersing and removing steps are carried out in an enclosed chamber.

5. The method of claim 2, wherein the step of lowering the density comprises reducing pressure and/or increasing temperature of the densified carbon dioxide composition.

6. The method of claim 2, wherein carbon dioxide in the densified carbon dioxide composition is present in a supercritical state.

7. The method of claim 2, wherein the carbon dioxide contains one or more of a co-solvent, a surfactant, and a co-surfactant.

8. The method of claim 2, wherein the polymeric material is a coating on one or more portions of the stent.

9. A method of producing a biocompatible stent for in vivo use, comprising:

provai stent having a portion thereof formed from polymeric material selected from the group consisting of: poly(glycolic acid), poly(D-lactic-co-glycolic acid), poly(L-lactic-co-glycolic acid), poly (D,L-lactic-co-glycolic acid), and a copolymer of poly(glycolic acid), poly(D-lactic-co-glycolic acid), poly(L-lactic-co-glycolic acid), or poly (D,L-lactic-co-glycolic acid), wherein the polymeric material contains one or more toxic materials;

immersing the polymeric material in a densified carbon dioxide composition such that the toxic materials are absorbed by the densified carbon dioxide composition, wherein pressure and/or temperature of the densified carbon dioxide composition is adjusted to selectively absorb toxic materials from the polymeric material;

removing the densified carbon dioxide composition containing the toxic materials from the polymeric material;

lowering the density of the removed densified carbon dioxide composition such that the toxic materials entrained therein become separated therefrom; and removing the separated toxic materials, such that the stent is suitable for in vivo use.

10. The method of claim 9, wherein the one or more toxic materials are selected from the group consisting of organic solvents (polar or non-polar), unpolymerized monomers, polymerization catalysts, oligomers, and polymerization initiators.

11. The method of claim 9, wherein the densified carbon dioxide composition is a liquid composition, and wherein the immersing and removing steps are carried out in an enclosed chamber.

12. The method of claim 9, wherein the step of lowering the density comprises reducing pressure and/or increasing temperature of the densified carbon dioxide composition.

13. The method of claim 9, wherein carbon dioxide in the densified carbon dioxide composition is present in a supercritical state.

14. The method of claim 9, wherein the carbon dioxide contains one or more of a co-solvent, a surfactant, and a co-surfactant.

15. The method of claim 9, wherein the polymeric material is a coating on one or more portions of the stent.

* * * * *